(12) United States Patent
Arndt et al.

(10) Patent No.: US 6,720,471 B1
(45) Date of Patent: Apr. 13, 2004

(54) ABSORBENT ARTICLES HAVING REDUCED REWET WITH DISTRIBUTION MATERIALS POSITIONED UNDERNEATH STORAGE MATERIAL

(75) Inventors: Silke Arndt, Darmstadt (DE); Bruno Johannes Ehrnsperger, Frankfurt (DE); Mattias Schmidt, Idstein (DE); Gary Dean Lavon, Oberursel (DE); Frank Neumann, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/674,053
(22) PCT Filed: Apr. 23, 1999
(86) PCT No.: PCT/IB99/00739
§ 371 (c)(1),
(2), (4) Date: Oct. 25, 2000
(87) PCT Pub. No.: WO99/55263
PCT Pub. Date: Nov. 4, 1999

(30) Foreign Application Priority Data

Apr. 28, 1998 (WO) ............................. PCT/US98/08515

(51) Int. Cl.⁷ .................................................. A61F 13/15
(52) U.S. Cl. ....................................... 604/367; 604/378
(58) Field of Search ........................ 604/378, 367–369, 604/374

(56) References Cited

U.S. PATENT DOCUMENTS

| 3,224,926 A | 12/1965 | Bernardin | 162/146 |
|---|---|---|---|
| 3,440,135 A | 4/1969 | Chung | 162/157 |
| 3,699,103 A | 10/1972 | Kiss | 260/210 |
| 3,770,731 A | 11/1973 | Jaeger | 260/248 |
| 3,932,209 A | 1/1976 | Chatterjee | 162/157 |
| 4,035,147 A | 7/1977 | Sangenis et al. | 8/116.4 |
| 4,041,951 A * | 8/1977 | Sanford | 128/287 |
| 4,673,402 A | 6/1987 | Weisman et al. | 604/368 |
| 4,695,278 A | 9/1987 | Lawson | 604/385 A |
| 4,798,603 A | 1/1989 | Meyer et al. | 604/378 |

(List continued on next page.)

FOREIGN PATENT DOCUMENTS

| EP | 0 809 991 A1 | 12/1997 | A61F/13/15 |
|---|---|---|---|
| EP | 0 887 059 A1 | 12/1998 | A61F/13/15 |
| GB | 2 296 511 A | 7/1996 | A61L/15/00 |
| WO | WO 95/26209 | 10/1995 | A61L/15/42 |
| WO | WO 97/34558 | 9/1997 | A61F/13/15 |
| WO | WO 97/34559 | 9/1997 | A61F/13/46 |
| WO | WO 98/03138 | 1/1998 | A61F/13/15 |
| WO | WO 98/43570 | 10/1998 | A61F/13/15 |
| WO | WO 98/43578 | 10/1998 | A61F/13/15 |
| WO | WO 99/25288 | 5/1999 | A61F/13/15 |
| WO | WO 99/25293 | 5/1999 | A61F/13/15 |
| WO | WO 99/62446 | 12/1999 | A61F/13/15 |
| WO | WO 00/06073 | 2/2000 | A61F/13/15 |

*Primary Examiner*—Weilun Lo
*Assistant Examiner*—Catherine L Anderson
(74) *Attorney, Agent, or Firm*—Edward J. Milbrada; Eileen L. Hughett; Ken K. Patel

(57) ABSTRACT

The present invention relates to an absorbent article, such as for use in hygienic applications, which has an ultimate fluid storage region, and a fluid distribution region positioned between the ultimate storage region and the garment oriented surface of the article, which is in fluid communication with the ultimate fluid storage region, whereby the ultimate fluid storage region comprises material which has a Capillary Sorption Desorption Capacity at 100 cm (CSDC 100) of at least 10 g/g. Further, the liquid distribution layer comprises material having a Capillary Sorption Absorption Height at 30% of its maximum capacity (CSAH 30) of at least 25 cm. The total article provides a reduced tendency for rewetting. Particularly suitable distribution material for the present invention can be foam materials, preferably polymeric foam derived from high internal phase water-in-oil emulsions.

27 Claims, 4 Drawing Sheets

U.S. PATENT DOCUMENTS

| | | | |
|---|---|---|---|
| 4,909,803 A | 3/1990 | Aziz et al. | 604/385.2 |
| 4,935,022 A | 6/1990 | Lash et al. | 604/368 |
| 4,968,312 A | 11/1990 | Khan | 604/388.1 |
| 4,976,819 A | 12/1990 | Minton | 162/9 |
| 4,988,345 A | 1/1991 | Reising | 604/368 |
| 4,990,147 A | 2/1991 | Freeland | 604/385.2 |
| 5,171,236 A | 12/1992 | Dreier et al. | 604/369 |
| 5,244,541 A | 9/1993 | Minton | 162/28 |
| 5,260,345 A | 11/1993 | DesMarais et al. | 521/148 |
| 5,269,755 A | 12/1993 | Bodicky | 604/53 |
| 5,304,614 A | 4/1994 | Winter et al. | 526/127 |
| 5,306,266 A | 4/1994 | Freeland | 604/385.1 |
| 5,360,420 A | 11/1994 | Cook et al. | 604/378 |
| 5,364,382 A | 11/1994 | Latimer et al. | 604/378 |
| 5,387,207 A * | 2/1995 | Dyer et al. | 521/64 |
| 5,397,318 A | 3/1995 | Dreier | 604/385.2 |
| 5,429,629 A | 7/1995 | Latimer et al. | 604/378 |
| 5,439,458 A | 8/1995 | Noel et al. | 604/378 |
| 5,454,800 A | 10/1995 | Hirt et al. | 604/378 |
| 5,514,121 A | 5/1996 | Roe et al. | 604/385.1 |
| 5,531,728 A | 7/1996 | Lash | 604/378 |
| 5,540,671 A | 7/1996 | Dreier | 604/385.2 |
| 5,554,142 A | 9/1996 | Dreier et al. | 604/385.1 |
| 5,560,222 A | 10/1996 | Perron | 62/435 |
| 5,560,878 A | 10/1996 | Dragoo et al. | 264/115 |
| 5,562,646 A | 10/1996 | Goldman et al. | 604/368 |
| 5,563,179 A | 10/1996 | Stone et al. | 521/64 |
| 5,599,335 A | 2/1997 | Goldman et al. | 604/368 |
| 5,643,588 A | 7/1997 | Roe et al. | 424/402 |
| 5,650,222 A | 7/1997 | DesMarais et al. | 442/370 |
| 5,653,703 A | 8/1997 | Roe et al. | 604/385.1 |
| 5,741,581 A | 4/1998 | DesMarais et al. | 428/284 |
| 5,744,506 A | 4/1998 | Goldman et al. | 521/64 |
| 5,895,379 A * | 4/1999 | Litchholt et al. | 604/368 |
| 5,968,025 A | 10/1999 | Roe et al. | 604/364 |
| 6,010,490 A | 1/2000 | Freeland et al. | 604/385.1 |
| 6,013,589 A | 1/2000 | DesMarais et al. | 442/370 |
| 6,024,209 A | 2/2000 | Nolte | 198/711 |
| 6,149,940 A | 11/2000 | Maggi et al. | 424/472 |
| 6,159,591 A * | 12/2000 | Beihoffer et al. | 428/327 |
| 6,168,584 B1 | 1/2001 | Allen et al. | 604/385.19 |

* cited by examiner

ABSORBENT ARTICLES HAVING REDUCED REWET WITH DISTRIBUTION MATERIALS POSITIONED UNDERNEATH STORAGE MATERIAL

GENERAL FIELD OF THE INVENTION

The present invention relates to absorbent articles which are primarily designed to receive and retain bodily discharges such as urine. Such articles are disposable hygiene articles like baby diapers, training pants, adult incontinence articles and the like.

BACKGROUND/PRIOR ART

Absorbent Articles for receiving and retaining bodily discharges such as urine or feces such as disposable diapers, training pants, adult incontinence articles are well known in the art, and significant effort has been spent against improving their performance. The ability to provide better performing absorbent articles such as diapers has been contingent on the ability to develop relatively thin absorbent cores or structures that can acquire and store large quantities of discharged body fluids, in particular urine, and in particular with minimized tendency for releasing received liquid back to wearer's skin.

In this regard, the use of certain absorbent polymers often referred to as "hydrogels," "superabsorbents" or "hydrocolloid" or "hydrogel forming" material has been particularly important. See, for example, U.S. Pat. No. 3,699,103 (Harper et al), issued Jun. 13, 1972, and U.S. Pat. No. 3,770,731 (Harmon), issued Jun. 20, 1972, that disclose the use of such absorbent polymers (hereafter "hydrogel-forming absorbent polymers") in absorbent articles. Indeed, the development of thinner diapers has been the direct consequence of thinner absorbent cores that take advantage of the ability of these hydrogel-forming absorbent polymers to absorb large quantities of discharged body fluids, typically when used in combination with a fibrous matrix. See, for example, U.S. Pat. No. 4,673,402 (Weisman et al), issued Jun. 16, 1987 and U.S. Pat. No. 4,935,022 (Lash et al), issued Jun. 19, 1990, that disclose dual-layer core structures comprising a fibrous matrix and hydrogel-forming absorbent polymers useful in fashioning thin, compact, nonbulky diapers. See also, U.S. Pat. No. 5,562,646 (Goldman et al.), issued Oct. 8, 1996 and U.S. Pat. No. 5,599,335 (Goldman et al.), issued Feb. 4, 1997, both of which relate to absorbent cores comprising regions of high concentrations of hydrogel-forming polymer, where the polymer forms a gel-continuous fluid transportation zone upon swelling.

In addition or alternatively to the use of hydrogel-forming absorbent polymers as the primary component in absorbent article storage structures, the use of polymeric foam materials derived from high internal phase water-in-oil emulsions ("HIPEs") has been identified. See, e.g., U.S. Pat. No. 5,260,345 (DesMarais et al.), issued Nov. 9, 1993, U.S. Pat. No. 5,387,207 (Dyer et al.) issued Feb. 7, 1995, and U.S. Pat. No. 5,560,222 (DesMarais et al.), issued Jul. 22, 1997.

Further disclosure is made of structures having a low capacity in the regions between the legs of the wearer such as in PCT application U.S. 97/05046, filed on Mar. 27, 1997, relating to the movement of fluid through certain regions of the article comprising materials having good acquisition and distribution properties to other regions comprising materials having specific liquid storage capabilities. In the PCT publication WO 98/43570, absorbent structures are described providing improved fit in combination with improved rewetting performance.

Further prior art aimed at providing material with improved fluid acquisition/distribution performance, such as by providing "surge management means" between the absorbent core and the topsheet, see for example EP-A-0.397.110 or EP-A-0.312.118.

Other documents disclose Absorbent articles with distribution layers underlying a storage layer which has a "fluid passage way" allowing fluid to pass from the surface to the underlying distribution layer without penetrating the absorbent materials in a microscopic view (see for example EP-A-0.565.606 or EP-A-0.343.940). Alternative designs were described, where the fluid was enabled to penetrate through the overlaying storage layer because this layer has a relatively low ultimate storage capacity, such as by having only small amounts of superabsorbent material, see for example EP-A-0.512.010.

In U.S. Pat. No. 5,454,800 (Hirt et al.), absorbent articles are disclosed, comprising at least a first and a second absorbent member in a layered arrangement, such that lower layer—for example a paper tissue—has better wicking properties than the first layer, which can be made from large pore materials such as co-form or air-laid tissue webs, or which can have gaps or apertures to allow fluid penetration into the under-laying layer.

Yet other articles describe the use of superabsorbent materials for being used in absorbent structures, whereby the materials exhibit a liquid permeability, expressed in "Saline Flow Conductivity", end as described in U.S. Pat. No. 5,599,335.

A further class of documents describe materials having improved fluid distribution properties, such as having high flux as disclosed in EP-A-0.809.991 or high wicking capability as disclosed in copending U.S. patent application Ser. No. 09/042418, filed Mar. 13, 1998 by T. DesMarais et al. titled "Absorbent materials for distributing aqueous liquids".

However, a problem with using distribution materials as described in such art is that a relatively high capillary absorbent pressure is required for the storage materials to drain the distribution materials, and to maintain good rewet performance of the article.

Thus, there is still a need to improve towards well performing articles, which provide good acquisition, good distribution without detrimentally affecting comfort of the wearer, such as providing low thickness, prevent a hard feel especially on the outer side of the article (often referred to as "poly-pockmarking"), which even might cause liquid to penetrate through. In particular, the combination of low thickness with small core sizes resulted in the need for overall "basis capacities", i.e. high amounts of fluid storage capacity per unit area.

OBJECTS OF THE INVENTION

Henceforth, it is an object of the present invention to provide an absorbent article with improvements in the above mentioned areas, in particular to provide an absorbent article which is easy to manufacture, even on conventional production lines.

It is a further object of the present invention to provide an absorbent article, which exploits the benefits of particularly suitable distribution materials with fluid storage materials or members of conventional type.

SUMMARY

The present invention is an absorbent article, such as for use in hygienic applications, which has an ultimate fluid storage region, and a fluid distribution region positioned between the ultimate storage region and the garment oriented surface of the article, which is in fluid communication with the ultimate fluid storage region, whereby the ultimate fluid storage region comprises material which has (1) a Capillary Sorption Desorption Capacity at 100 cm (CSDC 100) of at least 10 g/g; which further has (2) a Capillary Sorption Desorption Capacity at 0 cm (CSDC 0) higher than said CSDC 100 and which thereby has (3) a Loosely Bound Liquid Capacity (LBLC) as the difference between (CSDC 0 and CSDC 100); and which has (4) a Capillary Sorption Desorption Release Height when 50% of said LBLC are released (CSDRH 50) of less than 60 cm. Further, the liquid distribution layer comprises material having a Capillary Sorption Absorption Height at 30% of its maximum capacity (CSAH 30) of at least 25 cm.

Additionally, the ultimate fluid storage region can have a SFC value of more than $25\times10^{-7}$ cm$^3$sec/g., preferably more than $70\times10^{-7}$ cm$^3$sec/g, more preferably more than $100\times10^{-7}$ cm$^3$sec/g, even more preferably more than $200\times10^{-7}$ cm$^3$sec/g, most preferably more than $400\times10^{-7}$ cm$^3$sec/g or even more than $1000\times10^{-7}$ cm$^3$sec/g.

In a further aspect, the present invention can have a fluid distribution region material having a CSAH 30 of at least 50 cm.

In yet another aspect, the fluid distribution region material has a CSDH 50 of less than 150 cm. Alternatively, the benefits of the fluid distribution material can be described by having a fluid permeability value at 50% saturation (k(50)), which is at least 15% of the permeability value at 100% saturation (k(100)), preferably more than 18%, even more preferably more than 25% and most preferably more than 35% of the permeability value at 100% saturation (k(100)).

In yet another aspect, the fluid distribution region material has a permeability at 100% saturation (k(100)) of at least 1 Darcy, preferably of at least 8 Darcy.

In a preferred embodiment of the present invention, the distribution region material has a expansion factor of at least 4, preferably of at least 5, more preferably of at least 8, and most preferably of at least 15.

Another preferred execution of the present invention has distribution region material having a Cumulative Flux value at 15 cm in the Vertical Wicking test of at least 0.02 g/cm$^2$/min, preferably more than 0.04, even more preferably of more than 0.07 g/cm$^2$/min, and most preferably more than 0.14 g/cm$^2$/min.

Suitable materials for being useful for the present invention as fluid distribution and/or storage component can be foam materials, preferably polymeric foam material, and even more preferably polymeric foam material which is derived from high internal phase water-in-oil emulsions.

Alternatively, the distribution region can comprise fibrous material, preferably chemically stiffened cellulose, and/or synthetic fibers. Optionally, the distribution material can be mechanically treated after formation.

The distribution region according to the present invention can be a single layer material or is comprised of several layers, can be of essentially homogeneous composition and/or density and/or basis weight.

The ultimate fluid storage region can comprise fibrous material, preferably, this region comprises superabsorbent materials. Preferably, these materials have a SFC of at least $50\times10^{-7}$ cm$^3$sec/g, preferably of at least $80\times10^{-7}$ cm$^3$sec/g more preferably of at least 100 cm$^3$sec/g, and even more preferably of at least 150 cm$^3$sec/g.

The ultimate fluid storage region can be essentially homogeneous in composition, and can be a single or multi-layered structure. Preferably, the storage region is essentially free of void, apertures, or gaps having an individual void, aperture or gap volume of more than 10 mm$^3$.

When the absorbent article of the present invention is sectioned into a crotch and one or more waist regions, the crotch region can have a lower ultimate fluid storage capability than one or more waist region together, preferably less than 49%, more preferably less than 41% and even more preferably less than 23% of the total core ultimate fluid storage capacity.

In yet another aspect, the present invention is an absorbent article which has a relatively low basis weight of the liquid storage member of less than 450 g/m$^2$, and for which the basis weight of the liquid storage member is essentially constant throughout it, such as by having the basis weight of the ultimate storage material in the crotch region differing by less than 20% (dry weight basis) throughout the article.

In yet another aspect the absorbent article according to the present invention has a length of the crotch region which is half of the length of the total absorbent core. In a preferred embodiment the ultimate fluid storage region covers a surface area of at least 1.2 times the surface area of said fluid distribution region.

DETAILED DESCRIPTION

Definitions

Figure 1:
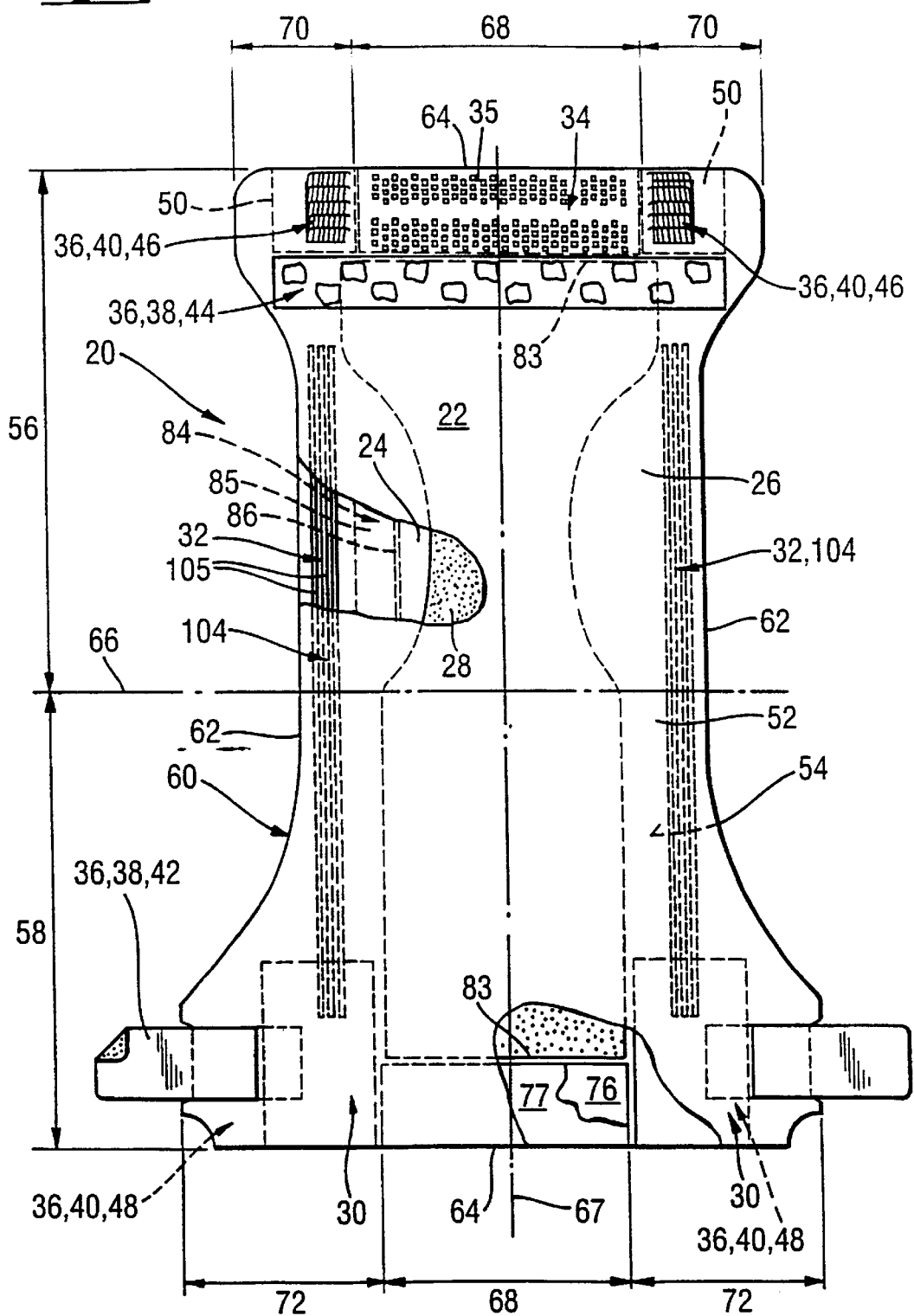
FIG. 1—Diaper as example for an absorbent article

As used herein, the term "absorbent articles" refers to devices which absorb and contain body exudates, and, more specifically, refers to devices which are placed against or in proximity to the body of the wearer to absorb and contain the various exudates discharged from the body. As used herein, the term "body fluids" includes, but is not limited to, urine, menses and vaginal discharges, sweat and feces.

The term "disposable" is used herein to describe absorbent articles which are not intended to be laundered or otherwise restored or reused as an absorbent article (i.e., they are intended to be discarded after use and, preferably, to be recycled, composted or otherwise disposed of in an environmentally compatible manner).

As used herein, the term "Z-dimension" refers to the dimension orthogonal to the length and width of the member, core or article. The Z-dimension usually corresponds to the thickness of the member, core or article. As used herein, the term "X-Y dimension" refers to the plane orthogonal to the thickness of the member, core or article. The X-Y dimension usually corresponds to the length and width, respectively, of the member, core or article.

As used herein, the term "absorbent core" refers to the component of the absorbent article that is primarily responsible for fluid handling properties of the article, including acquiring, transporting, distributing and storing body fluids. As such, the absorbent core typically does not include the topsheet or backsheet of the absorbent article.

As used herein, the term "absorbent member" refers to the components of the absorbent core that typically provide one or more fluid handling functionality, e.g., fluid acquisition, fluid distribution, fluid transportation, fluid storage, etc. The absorbent member can comprise the entire absorbent core or only a portion of the absorbent core, i.e., the absorbent core can comprise one or more absorbent members. The "storage absorbent member" is the absorbent member component(s) of the absorbent core that function primarily to ultimately store absorbed fluids. As discussed above, the storage absorbent member may also distribute fluid as a result of its vertical wicking capability.

As used herein, the terms "region(s)" or "zone(s)" refer to portions or sections of the absorbent member.

As use herein the term "layer" refers to an absorbent member whose primary dimension is X-Y, i.e., along its length and width. It should be understood that the term layer is not necessarily limited to single layers or sheets of material. Thus the layer can comprise laminates or combinations of several sheets or webs of the requisite type of materials. Accordingly, the term "layer" includes the terms "layers" and "layered".

For purposes of this invention, it should also be understood that the term "upper" refers to absorbent members, such as layers, that are nearest to the wearer of the absorbent article during use, and typically face the topsheet of an absorbent article; conversely, the term "lower" refers to absorbent members that are furthermost away from the wearer of the absorbent article and typically face the backsheet.

All percentages, ratios and proportions used herein are calculated by weight unless otherwise specified.

Absorbent Articles—General Description (Fig.1)

An absorbent article generally comprises:
an absorbent core (which may consist of sub-structures or absorbent members);
a fluid pervious topsheet;
a substantially fluid impervious backsheet;
optionally further features like closure elements or elastification.

FIG. 1 is a plan view of an exemplary embodiment of an absorbent article of the invention which is a diaper.

The diaper 20 is shown in FIG. 1 in its flat-out, uncontracted state (i.e. with elastic induced contraction pulled out except in the side panels wherein the elastic is left in its relaxed condition) with portions of the structure being cut-away to more clearly show the construction of the diaper 20 and with the portion of the diaper 20 which faces away from the wearer, the outer surface 52, facing the viewer. As shown in FIG. 1, the diaper 20 comprises a liquid pervious topsheet 24, a substantially liquid impervious backsheet 26 joined with the topsheet 24, and an absorbent core 28 positioned between the topsheet 24 and the backsheet 26; elasticized side panels 30; elasticized leg cuffs 32; an elastic waist feature 34; and a closure system comprising a dual tension fastening system generally multiply designated as 36.

The topsheet is preferably compliant, soft feeling, and non-irritating to the user's skin. Further, the topsheet is liquid pervious, permitting liquids (e.g., menses and/or urine) to readily penetrate through its thickness. A suitable topsheet may be manufactured from a wide range of materials such as woven and nonwoven materials (e.g., a non-woven web of fibers); polymeric materials such as apertured formed thermoplastic films, apertured plastic films, and hydroformed thermoplastic films; porous foams; reticulated foams; reticulated thermoplastic films; and thermoplastic scrims. Suitable woven and nonwoven materials can be comprised of natural fibers (e.g., wood or cotton fibers), synthetic fibers (e.g., polymeric fibers such as polyester, polypropylene, or polyethylene fibers) or from a combination of natural and synthetic fibers. The polymers used can be hydrophilic by their nature, can be rendered hydrophilic by addition of suitable surfactants, either applied to the surface of the polymers, or incorporated into the polymers, or such polymers can be (and kept) hydrophobic. When the topsheet comprises a nonwoven web, the web may be manufactured by a wide number of known techniques. For example, the web may be spunbonded, carded, wet-laid, melt-blown, hydroentangled, combinations of the above, or the like. The topsheet can comprise further materials, such as lotions or emmolients, such as described in EP-A-0.794.804.

The backsheet is impervious to liquids (e.g., menses and/or urine) and is preferably manufactured from a thin plastic film, although other flexible liquid impervious materials may also be used. As used herein, the term "flexible" refers to materials which are compliant and will readily conform to the general shape and contours of the human body. The backsheet prevents the exudates absorbed and contained in the absorbent core from wetting articles which contact the absorbent article such as bedsheets, pants, pajamas and undergarments. The backsheet may thus comprise a woven or nonwoven material, polymeric films such as thermoplastic films of polyethylene or polypropylene, or composite materials such as a film-coated nonwoven material. A suitable backsheet is a polyethylene film having a thickness of from about 0.012 mm (0.5 mil) to about 0.051 mm (2.0 mils). Exemplary polyethylene films are manufactured by Clopay Corporation of Cincinnati, Ohio, under the designation P18-1401 and by Tredegar Film Products of Terre Haute, Indiana, under the designation XP-39385. The backsheet is preferably embossed and/or matte finished to provide a more clothlike appearance. Further, the backsheet may permit vapors to escape from the absorbent core (i.e., the backsheet is breathable) while still preventing exudates from passing through the backsheet. Such a moisture vapor permeable backsheet can comprises materials such as microporous films or film laminates, nonwovens, including coated non-wovens, plasma treated non-wovens and the like, monolithic films, laminates or formed films, optionally having apertures not allowing omni-directional liquid pass through, such as slanted cones and the like, or combinations thereof. For such backsheets, a number of materials are commercially available, such as PEBAX® from Elf Atochem, France; ESTANE ®, from BF Goodrich, U.S.; Exxon Exxair® XFB-100W from Exxon Chemical Company of Buffalo Grove, Ill. U.S.; DuPont Hytrel® Film blend #P18-3097 or DuPont Hytrel® Film blend #P18-3096, the latter two available from Clopay Corporation, Cincinnati, Ohio, U.S. Within these kinds of films, the type of so called "monolithic film" are particularly preferred for being used in articles according to the present invention. Once such materials have picked up a certain amount of water, their permeability for water can actually increase. Thus, such materials can be particularly useful for designs with a liquid distribution layer in direct contact and in liquid communication with such materials, whereby these films are readily wetted by the liquid discharged to the article, and this is happening—due to the spreading and distribution properties of the distribution region—over a relatively large are of the absorbent article.

The dual tension fastening system 36 preferably comprises a primary fastening system 38 and a waist closure system 40. The primary fastening system 38 preferably comprises a pair of securement members 42 and a landing member 44. The waist closure system 40 is shown in FIG.

1 to preferably comprise a pair of first attachment components 46 and a second attachment component 48. The diaper 20 also preferably comprises a positioning patch 50 located subjacent each first attachment component 46.

The diaper 20 is shown in FIG. 1 to have an outer surface 52 (facing the viewer in FIG. 1), an inner surface 54 opposed to the outer surface 52, a first waist region 56, a second waist region 58 opposed to the first waist region 56, and a periphery 60 which is defined by the outer edges of the diaper 20 in which the longitudinal edges are designated 62 and the end edges are designated 64. The inner surface 54 of the diaper 20 comprises that portion of the diaper 20 which is positioned adjacent to the wearer's body during use (i.e. the inner surface 54 generally is formed by at least a portion of the topsheet 24 and other components joined to the topsheet 24). The outer surface 52 comprises that portion of the diaper 20 which is positioned away from the wearer's body (i.e. the outer surface 52 generally is formed by at least a portion of the backsheet 26 and other components joined to the backsheet 26). The first waist region 56 and the second waist region 58 extend, respectively, from the end edges 64 of the periphery 60 to the lateral centerline 66 of the diaper 20. The waist regions each comprise a central region 68 and a pair of side panels which typically comprise the outer lateral portions of the waist regions. The side panels positioned in the first waist region 56 are designated 70 while the side panels in the second waist region 58 are designated 72. While it is not necessary that the pairs of side panels or each side panel be identical, they are preferably mirror images one of the other. The side panels 72 positioned in the second waist region 58 can be elastically extensible in the lateral direction (i.e. elasticized side panels 30). (The lateral direction (x direction or width) is defined as the direction parallel to the lateral centerline 66 of the diaper 20; the longitudinal direction (y direction or length) being defined as the direction parallel to the longitudinal centerline 67; and the axial direction (Z direction or thickness) being defined as the direction extending through the thickness of the diaper 20).

FIG. 1 shows a specific execution of the diaper 20 in which the topsheet 24 and the backsheet 26 are unitary across the core and the chassis region and have length and width dimensions generally larger than those of the absorbent core 28. The topsheet 24 and the backsheet 26 extend beyond the edges of the absorbent core 28 to thereby form the periphery 60 of the diaper 20. The periphery 60 defines the outer perimeter or, in other words, the edges of the diaper 20. The periphery 60 comprises the longitudinal edges 62 and the end edges 64.

While each elasticized leg cuff 32 may be configured so as to be similar to any of the leg bands, side flaps, barrier cuffs, or elastic cuffs described above, it is preferred that each elasticized leg cuff 32 comprise at least an inner barrier cuff 84 comprising a barrier flap 85 and a spacing elastic member 86 such as described in the above-referenced U.S. Pat. No. 4,909,803. In a preferred embodiment, the elasticized leg cuff 32 additionally comprises an elastic gasketing cuff 104 with one or more elastic strands 105, positioned outboard of the barrier cuff 84 such as described in the above-references U.S. Pat. No. 4,695,278.

The diaper 20 may further comprise an elastic waist feature 34 that provides improved fit and containment. The elastic waist feature 34 at least extends longitudinally outwardly from at least one of the waist edges 83 of the absorbent core 28 in at least the central region 68 and generally forms at least a portion of the end edge 64 of the diaper 20. Thus, the elastic waist feature 34 comprises that portion of the diaper at least extending from the waist edge 83 of the absorbent core 28 to the end edge 64 of the diaper 20 and is intended to be placed adjacent the wearer's waist. Disposable diapers are generally constructed so as to have two elastic waist features, one positioned in the first waist region and one positioned in the second waist region.

The elasticized waist band 35 of the elastic waist feature 34 may comprise a portion of the topsheet 24, a portion of the backsheet 26 that has preferably been mechanically stretched and a bi-laminate material comprising an elastomeric member 76 positioned between the topsheet 24 and backsheet 26 and resilient member 77 positioned between backsheet 26 and elastomeric member 76.

This as well as other components of the diaper are given in more detail in WO 93/16669 which is incorporated herein by reference.

While it is preferred to have a topsheet as the material nearest the wearer's skin, it is not necessary. It is contemplated that a suitable absorbent core configuration could be used without a topsheet and still produce desirable results such as comfort and absorbency as well as simplicity in manufacturing and material cost savings. For example, the body-side surface of the absorbent core itself could be made of liquid pervious, soft, compliant, non-irritating materials that substitute for a separate topsheet. Such an absorbent core would only need to be used in combination with a backsheet to provide for comfort and absorbency in an absorbent article.

Regions of Absorbent Articles and Their Relative Arrangement

Generally, absorbent hygienic articles are intended for being worn around the lower end of the body torso. It is an essential design feature of these articles to cover the regions of the body where the discharges occur ("discharge regions"), which extend around the respective body openings. The respective zones of the absorbent article covering the discharge regions are correspondingly referred to as "loading zones". Thus during use, the articles are generally arranged on the wearer such that they extend (for a standing position of the wearer) from the crotch between the legs upwards, both in the front and the back of the wearer.

Generally, such articles have a length dimension exceeding their width dimension, whereby the article is worn such that the axis of the length dimension is aligned with the height direction of the wearer when standing, whilst the width direction of the article is aligned with a line extending from left to right of the wearer.

Because of the anatomy of the human wearer, the space between the legs of the wearer generally confines the space available for the article in this region. For good fit, an absorbent article should be designed such that it fits well in the crotch region. If the width of the article is excessively wide relative to the crotch width of the wearer, the article may be deformed, which might results in deteriorated performance, and reduced wearers comfort.

The point, where the article has its smallest width to fit best between the legs of the wearer then coincides with the point on the wearer, where the distance between the legs is the narrowest, and is—for the scope of the present invention—referred to as the "crotch point".

If the crotch point of an article is not obvious from its shape, it can be determined by placing the article on a wearer of the intended user group (e.g. a toddler) preferably in a standing position, and then placing an extensible filament around the legs in a figure eight configuration. The point in the article corresponding to the point of intersection of the filament is deemed to be the crotch point of the article and consequently also of the absorbent core being affixed within this article.

Whilst this crotch point of the article is often in the middle of the article (in longitudinal direction) this is not necessarily the case. It can very well be, that the part of the article which is intended to be worn in the front is smaller than the back (or rear) part—either in its length dimension, or width, or both, or surface area. Also, the crotch point does not need to be positioned in the middle of the absorbent core, in particular when the absorbent core is not placed longitudinally centered within the article.

The crotch region is the area surrounding the crotch point, so as to cover the respective body openings, respectively discharge regions. Unless otherwise mentioned, this region extends over a length of 50% of the total core length (which, in turn is defined as the distance between the front and rear waist edges of the core, which might be approximated by straight lines perpendicular to the longitudinal center line). If the crotch point is positioned in the middle of the article, then the crotch region starts (when counting from the front core edge) at 25% of total length and extends up to 75% of the total core length. Or, the front and the rear quarter of the length of the absorbent core do not belong to the crotch region, the rest does.

The crotch region length being 50% of the total absorbent core length has been derived for baby diapers, where it has been confirmed that this is a suitable means to describe the fluid handling phenomena. If the present invention is applied in articles having drastically different dimensions, it might become necessary to reduce these 50% (as in the case for Severe Incontinence articles) or to increase this ratio (as in the case for Ultra Light or Light Incontinence articles). In more general terms, this crotch region of the article should not extend much beyond the discharge region of the wearer.

If the crotch point is positioned offset from the mid-point of the article, the crotch region still covers 50% of the total article length (in longitudinal direction), however, not evenly distributed between front and back, but proportionally adjusted to this off-set.

As an example for an article having a total core length of 500 mm, and having a crotch point which is positioned centered, the crotch region will extend from 125 mm away from the front edge up to 375 mm away from front edge. Or, if the crotch point lies 50 mm offset towards the front core edge, (i.e. being 200 mm away from front core edge), the crotch region extends from 100 mm to 350 mm.

In general terms, for an article having a total core length of $L_c$, a crotch point being at a distance $L_{cp}$ away from the front core edge, and a crotch zone length of $L_{cz}$, the front edge of said crotch zone will be positioned at a distance $$L_{fecz}=L_{cp}*(1-0.5L_{cz}/L_{cp}).$$

For example the absorbent article can be a baby diaper, for being worn by toddlers (i.e. of about 12 to 18 kg baby weight) whereby the size of the article in the trade is generally referred to as MAXI size. Then the article has to be able to receive and retain both fecal materials and urine, whereas for the context of the present invention the crotch region has to be capable to primarily receive urine loading.

The total area and size of the crotch region is—of course—also depending on the respective width of the absorbent core, i.e. if the core is narrower in the crotch region than outside the crotch region, the crotch region can have a smaller area (surface) than the remaining area of the absorbent core.

Whilst it can be contemplated, that the boundaries between crotch region and the rest of the article can also be curvilinear, they are approximated within the present description to be straight lines, perpendicular to the longitudinal axis of the article.

The "crotch region" is further confined by the width of the core in this respective region, and the "crotch region area" by the surface as being defined by the crotch region length and the respective width.

As a complementary element to the crotch region, the absorbent core also comprises at least one but mostly two waist region(s), extending towards the front and/or the rear of the absorbent core outside the crotch region.

The various elements of the absorbent article and especially of the absorbent core can further be distinguished by their functionality.

Thereby, the region being closest to the loading point of the articles needs generally to ensure that the body exudates which are to be absorbed by the article are sufficiently quickly acquired so as to not remain on the surface of the article, where it might have too much undesired contact with the wearers skin. This region is often referred to as acquisition region.

Another region can be considered where the received body exudates are to be ultimately stored. This can be done in one region, which might be directly adjacent to the acquisition region, or this might be done primarily in a region somewhat distant from the acquisition region. Also, there can be more than one storage region, either in direct contact with each other (such as when placing two storage material layers on top of each other), or which can have no direct contact with each other (such as when placing each one storage region in the front and back parts of the article).

In any of the above cases, it can be desirable to have a further region, which has a primary functionality of fluid distribution, i.e. transporting the fluid primarily in x,y direction of the article, such as from the acquisition region to the storage region or regions.

In an absorbent article, the regions can be combined in one unitary and homogeneous structure or material. More preferably, however, at least some of the regions have different fluid handling properties different so as to be better adapted for their specific functionality. Often it is preferred to design the regions from materials having different properties.

For the particularly preferred designs according to the present invention, there must be at least one fluid storage region, and at least one other fluid acquisition/distribution region.

Each of the regions can have various shapes, such as being flat, (i.e. having essentially an x,y extension with essentially constant thickness dimension), or three-dimensionally shaped. Further, these regions can be arranged in various relative positions to each other, such as being layered, or circumscribing in x,y direction each other.

Preferred executions of the article comprising the various region have these arranged such that they have only little negative impact on the comfort of the wearer, and ideally no negative impact at all. This has to be considered for the article in its unloaded ("dry") state, as well as in its loaded state. For the latter a particularly preferred execution has a small width dimension in the crotch region, and also has relatively lower fluid storage capability in this region, so as to not increase the bulk between the legs even for a loaded article.

The various regions must be in fluid communicating contact with each other. i.e. there must be the possibility of the body exudates to move from the acquisition zone to the storage zone, and doing so by moving through the distribution region, if present.

Whilst the respective regions are referred to by their primary functionality, they generally also have at least to a certain degree other functionality. Thus, a fluid absorbent storage region may also have a fluid distribution functionality, and a fluid acquisition/distribution region may have some fluid retention capability.

Design Capacity and Ultimate Storage Capacity

In order to be able to compare absorbent articles for varying end use conditions, or differently sized articles, the "design capacity" has been found to be a suitable measure.

For example, babies are representing a typical usage group, but even within this group the amount of urine loading, frequency of loading, composition of the urine will vary widely from smaller babies (new-born babies) to toddlers on one side, but also for example among various individual babies.

Another user group may be larger children, still suffering from a certain form of incontinence.

Also, incontinent adults can use such articles, again with a wide range of loading conditions, generally referred to as light incontinence ranging up to severe incontinence.

Whilst the man skilled in the art will readily be able to transfer the teaching to other sizes for further discussion, focus will be put on the toddler sized babies. For such user, urine loading of up to 75 ml per voiding, with on an average of four voidings per wearing period resulting in a total loading of 300 ml, and voiding rates of 15 ml/sec have been found to be sufficiently representative.

Henceforth, such articles being able to cope with such requirements should have the capability of picking up such amounts of urine, which will be referred to for the further discussion as "design capacity".

These amounts of fluids have to be absorbed by materials which can ultimately store the bodily fluids, or at least the aqueous parts of these, such that—if any—only little fluid is left on the surface of the article towards the wearers skin. The term "ultimate" refers in one respect to the situation as in the absorbent article at long wearing times, in the other respect to absorbent materials which reach their "ultimate" capacity when being equilibrated with their environment. This can be in such an absorbent article under real in-use conditions after long wearing times, or this also can be in a test procedure for pure materials or material composites. As many of the processes under consideration have asymptotic kinetic behavior, one skilled in the art will readily consider "ultimate" capacities to be reached when the actual capacity has reached a value sufficiently close to the asymptotic endpoint, e.g. relative to the equipment measurement accuracy.

As an absorbent article can comprise materials which are primarily designed to ultimately store fluids, and other materials which are primarily designed to fulfill other functions such as acquisition and/or distribution of the fluid, but may still have a certain ultimate storage capability, suitable core materials according to the present invention are described without attempting to artificially separate such functions. Nonetheless, the ultimate storage capacity can be determined for the total absorbent core, for regions thereof, for absorbent structures, or even sub-structures, but also for materials as being used in any of the previous.

As discussed in the above for varying the dimensions of the article, one skilled in the art will be able to readily adopt the appropriate design capacities for other intended user groups.

Absorbent Members

Apart from looking at the various regions of the absorbent core from a functionality point of view, it is often desirable to consider an absorbent core to be composed of one or more absorbent members or structures, which might consist of sub-structures, such than an absorbent core can be considered to be composed of one or—as in most cases of modern absorbent article designs several different "materials". Within the context of the present invention, a material forming an absorbent member is an element which can be tested for its "material properties", independent of whether the material is a "pure"material (e.g. a particle of superabsorbent material), an accumulation of homogeneous material (e.g. a mass of cellulose fibers, or a foam structure, or a mass of superabsorbent particles), a mixture of two or more pure materials or material accumulations (e.g. a mixture of superabsorbent particles having different properties, or a blend of superabsorbent particles and cellulosic fibers); or a further arrangement of several materials forming a distinctable absorbent member (such as a two layer composite).

Hence, it will be possible to assess the fluid handling properties of a "fluid handling member", and for certain members it will also be possible to assess the properties of the substructures or materials comprised therein.

The functional regions as described above can be formed out of the same material (for example cellulose web, or a mixture of cellulose and superabsorbent material), whereby the different regions are defined for example by varying densities. More preferably, such different properties can be achieved by using different members and/or materials, allowing a wider range of design flexibility by allowing hydrophilicity, or pore size or other properties relevant for fluid handling to be varied over a much wider range.

Figure 4:
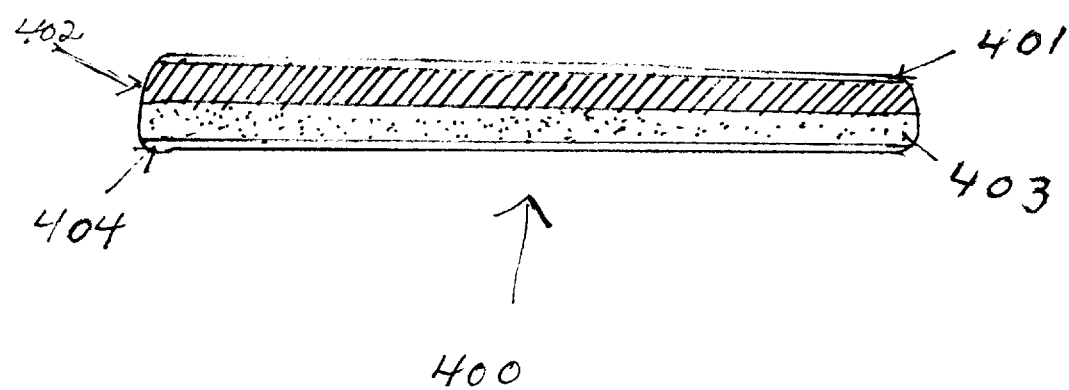
FIG. 4—Cross-section of an embodiment of an absorbent article according to the instant invention.

Referring to the embodiment of FIG. 4, which illustrates a cross-section, the article 400 according to the present invention is characterized in that the fluid distribution region 403 is positioned underneath the fluid storage region 402. This means, that—when viewing the relative positioning of these two regions during the intended use of the article—the storage region is positioned closer towards the wearer during use. Or, if the absorbent article has a topsheet 401, which is intended to form the wearer oriented surface of the article, and a backsheet 404, which forms the garment oriented surface of the article, the storage region is positioned underneath the topsheet, the distribution is positioned underneath the storage region, and the backsheet is positioned underneath the distribution region. This also means, that the liquid as released by the wearer, will follow a z-directionally oriented flow path through the storage region, before it will reach the distribution region. There, the fluid will be transported through the distribution member to other regions of the article, namely to regions which are laterally and/or longitudinally spaced away from the loading point of the article.

Often, but not necessarily, the regions are in the form of layers, such a storage layer overlaying a layer of distribution material. These layers can be, but not necessarily have to be of the same x- and/or y- dimensions, however, the upper storage layer or regions has to cover the distribution region at least in the loading region, i.e. the region where the body exudates contact the absorbent article.

A particularly preferred arrangement of the distribution and the storage regions is such that the storage region has a non-uniform basis capacity distribution, such that the crotch region of the wearer has a lower capacity than the end regions. Such basis capacity can be achieved by a change in overall basis weight profile, i.e. by putting more absorbent material towards the end regions. Or, it could be achieved by positioning material (or material mixture) with a higher absorbency per weight unit towards the end regions.

Capillary Sorption

The fluid handling properties of the various members or materials useful for the present invention are heavily depending on the fluid absorption and desorption properties. The so called Capillary Sorption Test is a very useful tool to determine various parameter relating to these properties. The test should be carried out according to the detailed description of the PCT application titled "Absorbent Articles with Distribution Materials positioned underneath storage materials" filed in the name of the present applicant on Apr. 28, 1998 as PCT application U.S. 98/08515, which is incorporated herein by reference.

Reporting

As has been set out in this test description, the following values can be calculated and are useful for the description of the performance of materials:

The Capillary Sorption Desorption Height at which the material has released x % of its capacity achieved at 0 cm (i.e. of CSAC 0), (CSDH x) expressed in cm;

The Capillary Sorption Absorption Height at which the material has absorbed y % of its capacity achieved at 0 cm (i.e. of CSAC 0), (CSAH y) expressed in cm;

The Capillary Sorption Absorbent Capacity at a certain height z (CSAC z) expressed in units of g {of fluid}/g {of material}; especially at the height zero (CSAC 0), and at heights of 35 cm, 40 cm, etc.

The Capillary Sorption Absorption Efficiency at a certain height z (CSAE z) expressed in %, which is the ratio of the values for CSAC 0 and CSAC z.

A further parameter relates to the amount of liquid, which is loosely bound in a materials, in particular in a distribution material. This Loosely Bound Liquid Capacity (LBLC) is determined by the difference of (1) the Capillary Sorption Desorption Capacity at 0 cm (CSDC 0), and (2) the Capillary Sorption Desorption Capacity at 100 cm (CSDC 100). Any liquid that is not released in a desorption experiment at a pressure of at least 100 cm is called Tightly Bound Liquid (TBLC). The TBLC of a material equals that CSDC100 of that material. It will also be readily understood, that the Capillary Sorption Desorption Capacity at 0 cm is substantially equivalent to the Capillary Sorption Absorption Capacity at 0 cm.

Accordingly, yet another parameter can be defined relating to the desorption pressure (i.e. height) when 50% of this LBLC is released. This is the Capillary Sorption Desorption Release Height when 50% of said LBLC are released (CSDRH 50).

If two materials are combined (such as the first being used as acquisition/distribution material, and the second being used as liquid storage material), the CSAC value (and hence the respective CSAE value) of the second material can be determined for the CSDH x value of the first material.

Distribution Region Requirements

Whilst the required properties of well functioning materials or members in one region are depending on properties of the absorbent members or materials in the other region, the following characteristics have been found to provide suitable distribution members.

Fluid distribution materials in the context of the present invention are materials for applications such as in absorbent articles, which are intended to support the fluid transport mechanisms in such articles. Such articles generally have two centerlines, a longitudinal and a transverse one. The term "longitudinal" as used herein, refers to a line axis or direction in the plane of the article, that is generally aligned with (e.g. approximately parallel to) a vertical plane which bisects a standing wearer of such an article into left and right body halves. The fluid transport mechanisms may then be required to effectively use absorbent material which can be spread in the article over a larger region than the loading regions, i.e. this region of the articles where bodily discharges are disposed onto the surface of the absorbent article. Such transport can occur through driving forces such as gravity, which will not allow fluid distribution against the direction of the gravity, and hence often not satisfy requirements as set out for absorbent articles, whereby fluid needs to be transported from the loading point, where discharged fluids are discharged onto the absorbent article, to other parts of the article, which are positioned "higher", i.e. upwards against the direction of gravity.

This wicking is generally achieved by exploiting capillary forces, and can be best assessed by testing the materials in the vertical orientation, i.e. positioning these along the direction of gravity.

Equally important, however, is the amount of fluid which has to be transported. Characteristic loading for baby diapers can be more than 300 ml of urine loading, in voidings often at 75 ml per voiding, and voiding rates of up to 15 ml/sec. Hence the need for the ability to transport significant amounts becomes obvious. There is, however, a further need for low material usage both due to economical use of materials and due to comfort and fit requirements for the wearer. Hence, preferred materials allow transport of large amounts of fluids in short times through a small cross section of such material. This can generally be expressed by the "Vertical Wicking Flux" parameter such as measured by Vertical Wicking Test as described hereinafter, being defined by the cumulative amount of fluid being transported to a given height through a certain cross-section of material in a certain time, expressed in $ml/cm^2/sec$, and by the time the fluid front penetrates up to a certain height in the material against gravity.

These parameters can be easiest determined by using the vertical wicking test, such as specified below, measuring the ability of a material to transport fluid through its internal voids (such as pores) at constancy or absence of external forces, such as gravity or centrifugal forces. Essentially, a specimen of the material is placed in a vertical position extending out of a fluid reservoir. The transport against the gravity can be monitored by measuring both the upward movement of the wetting front and the amount of fluid which is picked up by the material.

Wicking height can be easily increased by decreasing the effective pore size of the distribution material, according to the generally known Lucas-Washburn relationship for capillary systems, which often has been applied to also approximate porous systems. For a given fluid—for example urine or menstrual fluid—and a certain material exhibiting a certain surface energy, the required capillary (or pore) diameter can be approximated to allow wicking up to a certain required height. Obviously, when aiming for large wicking heights, this relation requires small capillary diameter.

However, such small capillaries are not able to handle high amounts fluid, and the cumulative flux for such fluids through such a material with small pores is significantly reduced. This is caused by the high internal friction (or low permeability) that is linked to small pores (according to the Hagen-Poisseuille relationship).

Thus, the preferred distribution material can be described by having a cumulative flux of more than $0.02\ g/cm^2/min$ at 15 cm height, preferably more than $0.04\ g/cm^2/min$, even more preferably of more than $0.07\ g/cm^2/sec$, and most preferably of more than $0.14\ g/cm^2/min$.

Whilst flux is one parameter to consider suitable distribution materials, the permeability of the webs is a further important property. Preferably, the distribution materials or members have a sufficiently open structure by having a permeability at 100% saturation, k(100), of a value of more than about 1 Darcy, preferably more than about 2 Darcy, even more preferably more than 8 Darcy or even more than 100 Darcy. Even further, these materials not only exhibit good permeability values when they are saturated, but they also when they are not completely saturated, i.e. have a permeability at 50% of their saturation, k(50), which is more than about 14% of the permeability at 100% saturation, k(100), preferably more than about 18%, even more preferably more than about 25% or even more than about 35% and/or a permeability at 30% of their saturation, k(30), which is more than about 3.5% of the permeability at saturation, even more preferably more than about 5%, or even more than 10%.

Certain materials suitable for the present invention have a specific behavior of being thin when being dry (such as during manufacturing of the article), and increasing in thickness when being wetted (such as being loaded with liquid during use). Such materials have preferably an expansion factor (i.e. the caliper of a layer of material compared in its dry state and in its wet state) of at least 4, preferably of at least 5 and even more preferably of at least 10, and even more preferably of at least 15. In a further aspect it is preferred that such materials also can reduce their caliper after being wetted such as during use, when the liquid is picked up by the ultimate liquid storage medium. Thus, these materials preferably re-collapse when being drained with the same factor as the expansion factor.

Further essential properties of the materials useful for the present invention can be assessed in the "Capillary Sorption Test" as described before, relating to the ability of a material to hold or release fluid as a function of the pressure acting on the fluid, such as gravitational forces.

In order to ensure, that the fluid can be readily transferred from the voids of the upper storage region to the distribution layer immediately after the gush, the fluid distribution materials useful for the present invention have the ability of absorbing 30% of their maximum capacity (i.e. the capacity at 0 cm height) at a height of at least 35 cm as measured in the capillary sorption test.

However, preferred executions of the distribution material do not hold the liquid too strongly, such that it can be released to the ultimate storage regions—either within the previously wetted region, which can the retain the liquid tightly in the smaller pore portion of the material, or in a more remote storage region, which has not been loaded with the liquid during the gush. Thus, the distribution material should exhibit a Capillary Sorption Desorption Height for 50% of its maximum capacity (i.e. the capacity at 0 cm height) of less than 150 cm.

Materials Suitable to Achieve Distribution Requirements

Fluid distribution members suitable for being used in the present invention, can comprise various materials and can be made by various processes. A suitable member can be a web comprising resilient fibers, which are formed into this web by well known processes, such as air-laying, or wetlaying and the like. A wide variety of resilient fibers can be envisaged to perform well in members according to the present invention. Apart from well know synthetic fibers such as being based on polyethyleneterephtalate, polyester, polyamine, resilient polyolefins or combinations thereof e.g. in bi-component fiber form, a particularly preferred fiber is a chemically-stiffened, twisted bulking cellulosic fiber.

Stiffened cellulose fibers can be prepared by internally crosslinking such fibers in relatively dehydrated form while or after such fibers are being or have been dried and defibrated (i.e., "fluffed") as described in U.S. patent application Ser. No. 304,925. It is not, however, meant to necessarily exclude other hydrophilic, chemically stiffened, twisted, and curled fibers from this invention, such other fibers being described in (but, not limited to) the previously mentioned U.S. Pat. Nos. 3,224,926, 3,440,135, 4,035,147, and 3,932,209. Other non-chemical means of providing stiffened, twisted, and curled cellulose fibers are also contemplated as being within the scope of the present invention, such as high consistency (generally greater than about 30%) mechanical treatment (e.g., frotapulping and/or refining, etc.). Such methods are described in greater detail in U.S. Pat. Nos. 4,976,819 and 5,244,541, issued Dec. 11, 1990 and Sep. 14, 1993, respectively, to Mary L. Minton and entitled "Pulp Treatment Methods".

Other preferred webs further can comprise a second type of fibers having a relatively high surface area. Whilst also synthetic fibers such as having a very small diameter ("microfibers") or having a special surface configuration are contemplated to be suitable, a presently preferred fiber for this high surface application is the eucalyptus family of wood pulp fibers. Eucalyptus provides desirable capillary pressure characteristics in combination with the chemically stiffened, twisted, and curled fibers and will not easily pass through the forming screen, as does a significant amount of the cellulose fines described below. Particularly suitable eucalyptus fibers include those of the eucalyptus grandis species.

When resilient fibers such as the crosslinked, twisted, stiffened fibers are combined with high surface area fibers as described above, the resulting web can have significantly reduced tensile strength, particular in a wet condition. Therefore, in order to facilitate processing and provide product-specific mechanical properties, in both wet and dry states, a binding means can be integrally incorporated into or onto the web. This can be done by adding the binding means to pulp prior to web formation, by applying the binding means to a wetlaid web after deposition on a forming wire, and before drying, after drying, or a combination thereof.

Alternatively to the fibrous webs as described hereinbefore, relatively open-celled polymeric foams can be used, in particular hydrophilic, flexible polymeric foam structures of interconnected open-cells.

For such foams, the mechanical strength of the foam can be such that, upon giving up its liquid, the foam collapses under the capillary pressures involved. The collapse process reduces the effective foam capacity by a substantial factor related to the density of the foam, as is described hereinafter. The collapse, if relatively uniform throughout the structure, also reduces the amount of liquid held in place at the point of liquid insult. In this regard, the strength of the foams is less than the capillary pressure exerted by the foams such that the foams will collapse when the aqueous liquids are removed by the storage component of the core. Capillary pressure is controlled herein primarily by adjusting foam cell size (which relates inversely to surface area per unit volume). Strength is controlled by the combination of crosslink density and foam density, which can be expressed as crosslink density per unit volume as defined hereinafter. The type of crosslinker and other comonomers can also be influential.

Polymeric foams useful herein are those which are relatively open-celled. The cells in such substantially open-celled foam structures have intercellular openings or "windows" that are large enough to permit ready liquid transfer from one cell to the other within the foam structure.

These substantially open-celled foam structures will generally have a reticulated character with the individual cells being defined by a plurality of mutually connected, three dimensionally branched webs. The strands of polymeric material making up these branched webs can be referred to as "struts". For purposes of the present invention, a foam material is "open-celled" if at least 80% of the cells in the foam structure that are at least 1 μm in size are in fluid communication with at least one adjacent cell.

In addition to being open-celled, these polymeric foams are sufficiently hydrophilic to permit the foam to absorb aqueous liquids. The internal surfaces of the foam structures are rendered hydrophilic by residual hydrophilizing surfactants and/or salts left in the foam structure after polymerization, or by selected post-polymerization foam treatment procedures, as described hereafter.

The extent to which these polymeric foams are "hydrophilic" can be quantified by the "adhesion tension" value exhibited when in contact with an absorbable test liquid. The adhesion tension exhibited by these foams can be determined experimentally using a procedure where weight uptake of a test liquid, e.g., synthetic urine, is measured for a sample of known dimensions and capillary suction specific surface area. Such a procedure is described in greater detail in the Test Methods section of U.S. Pat. No. 5,387,207 (Dyer et al.) issued Feb. 7, 1995, which is incorporated by reference. Foams which are useful as distribution materials of the present invention are generally those which exhibit an adhesion tension value of from about 15 to about 65 dynes/cm, more preferably from about 20 to about 65 dynes/cm, as determined by capillary suction uptake of synthetic urine having a surface tension of 65±5 dynes/cm.

The skilled artesian will recognize that a wide variety of polymeric open celled foams are useful for the present invention. The following two chapters describe two generic classes of above foams which are particularly preferred for use in the present invention with the first class comprising foams that have especially high flux and the second class are foams having particularly high CSAH30. Other polymeric foams having combination of both properties might be especially useful.

Polymeric Distribution Foams Having a High Wicking Flux

An important aspect of these foams is their glass transition temperature (Tg). The Tg represents the midpoint of the transition between the glassy and rubbery states of the polymer. Foams that have a higher Tg than the temperature of use can be very strong but can also be very rigid and potentially prone to fracture. Such foams also tend to creep under stress and be poorly resilient when used at temperatures colder than the Tg of the polymer. The desired combination of mechanical properties, specifically strength and resilience, typically necessitates a fairly selective range of monomer types and levels to achieve these desired properties.

For distribution foams useful for the present invention, the Tg should be as low as possible, so long as the foam has acceptable strength. Accordingly, monomers are selected as much as possible that provide corresponding homopolymers having lower Tg's.

The shape of the glass transition region of the polymer can also be important, i.e., whether it is narrow or broad as a function of temperature. This glass transition region shape is particularly relevant where the in-use temperature (usually ambient or body temperature) of the polymer is at or near the Tg. For example, a broader transition region can mean transition is incomplete at in-use temperatures. Typically, if the transition is incomplete at the in-use temperature, the polymer will evidence greater rigidity and will be less resilient. Conversely, if the transition is completed at the in-use temperature, then the polymer will exhibit faster recovery from compression. Accordingly, it is desirable to control the Tg and the breadth of the transition region of the polymer to achieve the desired mechanical properties. Generally, it is preferred that the Tg of the polymer be at least about 10° C. lower than the in-use temperature. (The Tg and the width of the transition region are derived from the loss tangent vs. temperature curve from a dynamic mechanical analysis (DMA) measurement, as described in U.S. Pat. No. 5,563,179 (Stone et al.) issued Oct. 8, 1996.)

Polymeric foams useful for the present invention can be described by a number of parameters.

Foams useful for the present invention are able to wick aqueous liquids to a significant height against the force of gravity, e.g., at least about 15 cm. The column of liquid held within the foam exerts a significant contractile capillary pressure. At a height determined by both the strength of the foam (in compression) and the surface area per unit volume of the foam, the foam will collapse. This height is the Capillary Collapse Pressure (CCP) expressed in cm at which 50% of the volume of the foam at zero head pressure is lost. Preferred distribution foams useful for the present invention will have a CCP of at least about 15 cm, more preferably at least about 20 cm, still more preferably at least about 25 cm or even at least about 70 cm. Typically, preferred distribution foams will have a capillary collapse pressure of from about 15 cm to about 80 cm, more preferably from about 20 cm to about 75 cm, still more preferably from about 25 to about 70 cm.

A feature that can be useful in defining preferred polymeric foams is the cell structure. Foam cells, and especially cells that are formed by polymerizing a monomer-containing oil phase that surrounds relatively monomer-free water-phase droplets, will frequently be substantially spherical in shape. These spherical cells are connected to each other by openings, which are referred to hereafter as holes between cells. Both the size or "diameter" of such spherical cells and the diameter of the openings (holes) between the cells are commonly used for characterizing foams in general. Since the cells, and holes between the cells, in a given sample of polymeric foam will not necessarily be of approximately the same size; average cell and hole sizes, i.e., average cell and hole diameters, will often be specified.

Cell and hole sizes are parameters that can impact a number of important mechanical and performance features of the, including the liquid wicking properties of these foams, as well as the capillary pressure that is developed within the foam structure. A number of techniques are available for determining the average cell and hole sizes of foams. A useful technique involves a simple measurement based on the scanning electron photomicrograph of a foam sample. The foams useful as absorbents for aqoueous liquids in accordance with the present invention will preferably have a number average cell size of from about 20 μm to about 60 μm, and typically from about 30 μm to about 50 μm, and a number average hole size of from about 5 μm to about 15 μm, and typically from about 8 μm to about 12 μm.

"Capillary suction specific surface area" is a measure of the test-liquid-accessible surface area of the polymeric network accessible to the test liquid. Capillary suction specific surface area is determined both by the dimensions of the cellular units in the foam and by the density of the polymer, and is thus a way of quantifying the total amount of solid surface provided by the foam network to the extent that such a surface participates in absorbency.

For purposes of this invention, capillary suction specific surface area is determined by measuring the amount of capillary uptake of a low surface tension liquid (e.g., ethanol) which occurs within a foam sample of a known mass and dimensions. A detailed description of such a procedure for determining foam specific surface area via the capillary suction method is set forth in the Test Methods section of U.S. Pat. No. 5,387,207 supra. Any reasonable alternative method for determining capillary suction specific surface area can also be utilized.

Distribution foams useful for the present invention will preferably have a capillary suction specific surface area of at least about 0.01 m$^2$/ml, more preferably at least about 0.03 m$^2$/ml. Typically, the capillary suction specific surface area is in the range from about 0.01 to about 0.20 m$^2$/ml, preferably from about 0.03 to about 0.10 m$^2$/ml, most preferably from about 0.04 to about 0.08 m$^2$/ml.

"Foam density" (i.e., in grams of foam per cubic centimeter of foam volume in air) is specified herein on a dry basis. The density of the foam, like capillary suction specific surface area, can influence a number of performance and mechanical characteristics of absorbent foams. These include the absorbent capacity for aqueous liquids and the compression deflection characteristics. Foam density will vary according to the state of the foam. Foams in the collapsed state obviously have higher density than the same foam in the fully expanded state. In general, foams in the collapsed state useful for the present invention have a dry density of about 0.11 g/cm$^3$.

Any suitable gravimetric procedure that will provide a determination of mass of solid foam material per unit volume of foam structure can be used to measure foam density. For example, an ASTM gravimetric procedure described more fully in the Test Methods section of U.S. Pat. No. 5,387,207 supra is one method that can be employed for density determination. Foam density pertains to the weight per unit volume of a washed foam free of emulsifiers, fillers, surface treatments such as salts, and the like. The foams useful for the present invention will preferably have dry densities of from about 8 mg/cm$^3$ to about 77 mg/cm$^3$, more preferably from about 11 mg/cm$^3$ to about 63 mg/cm$^3$ still more preferably from about 13 mg/cm$^3$ to about 48 mg/cm$^3$.

Details of polymeric foam materials useful for the present invention are described in detail in the description of the PCT application titled "Absorbent Articles with Distribution Materials positioned underneath storage materials" filed in the name of the present applicant on Apr. 28, 1998 as PCT application U.S. 98/08515, which is incorporated herein by reference.

Storage Region Member Requirements

In addition to the requirements for the lower distribution region, the storage region has to satisfy certain requirements.

First, the storage region must be able to firmly retain the liquid tightly bound, such as described by the term of ultimate storage capacity, or in terms of the Capillary Sorption Test parameter, by having a Capillary Sorption Desorption Capacity at 100 cm height of at least 10 g/g (dry basis). In order to allow readily releasing of the loosely bound fluid to the underlying distribution layer, the fluid storage region can comprise a material having a Capillary Sorption Desorption Release Height when 50% of the Loosely Bound Liquid Capacity are released (i.e. the CSDRH 50 as defined in the Capillary Sorption Test) of less than 60 cm, preferably less, such as less than 50 cm, even more preferably less than 40 cm, and most preferably less than 30 cm and even less than 20 cm.

A further important property can be measured by the storage member Saline Flow Conductivity (SFC) test. This is relevant for allowing the fluid to flow through the storage member material, particularly when the storage member has no apertures, gaps, or macro voids which could serve as channels for the fluid to by pass the material. Rather, the benefits of the present invention allows the fluid to penetrate through the bulk material of the storage member. Thus, the storage region members or materials must be permeable so as to allow liquid pass through, and this fluid permeability should be maintained from the beginning of the wetting through the end, possibly over several urination cycles. The specific design arrangement of the present invention requires, that the fluid passes through the storage region before it reaches the distribution region to be further distributed into the x, and or y direction of the article. Henceforth, it is a key requirement for the storage region to be sufficiently permeable to such fluids in the plane of fluid transport (x,y direction) in addition of having a high transplanar permeability.

Thus, preferred storage members should exhibit values of at least 25×10-7 cm3sec/g, preferably more than 70×10-7 cm$^3$sec/g, even more preferably more than 100×10-7 cm$^3$sec/g or even more than 200×10-7 cm$^3$sec/g, and most preferably more than about 400×10-7 cm$^3$sec/g or even more than 1000×10-7 cm$^3$sec/g.

In addition to the superabsorbent material, the storage region can comprise other materials or members, making a permeable member. It is important, that such members release the fluid readily, either to the distribution layer so as to allow distribution throughout the total absorbent article, or to the increased fluid storage capacity in the ends of the article, or to the superabsorbent of the storage region itself.

Materials to Achieve Storage Region Requirements

Hydrogel-Forming Absorbent Polymers

The storage absorbent members of the present invention comprise at least one hydrogel-forming absorbent polymer (also referred to as hydrogel-forming polymer "Superabsorbent material", or "supersorber"). Hydrogel-forming polymers useful in the present invention include a variety of water-insoluble, but water-swellable polymers capable of absorbing large quantities of liquids. Such hydrogel-forming polymers are well known in the art and any of these materials are useful in the absorbent members of the present invention. Details of useful Hydrogel forming absorbent polymers are described in more detail in the description of the PCT application titled "Absorbent Articles with Distribution Materials positioned underneath storage materials" filed in the name of the present applicant on Apr. 28, 1998 as PCT application U.S. Ser. No. 98/08515, which is incorporated herein by reference.

The hydrogel-forming polymer component may also be in the form of a mixed-bed ion-exchange composition comprising a cation-exchange hydrogelforming absorbent polymer and an anion-exchange hydrogel-forming absorbent polymer. Such polymers can have a particularly well balanced property profile of their absorbency properties, namely Performance Under Pressure values, Saline Flow Conductivity values, and Free Swell Rate. Such mixed-bed ion-exchange compositions as well as the appropriate methods to determine such parameter, are described in, e.g., U.S. patent application Ser. No. 09/003565, filed Jan. 7, 1998 by Hird, et al. titled "ABSORBENT POLYMER COMPOSITIONS HAVING HIGH SORPTION CAPACITIES UNDER AN APPLIED PRESSURE"; U.S. patent application Ser. No. 09/003905, filed Jan. 7, 1998 by Ashraf, et al. titled "ABSORBENT POLYMER COMPOSITIONS WITH HIGH SORPTION CAPACITY AND HIGH FLUID PERMEABILITY UNDER AN APPLIED PRESSURE"; and U.S. patent application Ser. No. 09/003918, filed Jan. 7, 1998 by Ashraf, et al. titled "ABSORBENT POLYMER COMPOSITIONS HAVING HIGH SORPTION CAPACITIES UNDER AN APPLIED PRESSURE AND IMPROVED INTEGRITY IN THE SWOLLEN STATE"); the disclosure of each of which is incorporated herein by reference. Materials particularly useful for the present invention exhibit high Performance Under Pressure and Saline Flow Conductivity values, and slow Free Swell Rates.

Such Free Swell Rates, as measured by the Free Swell rate method as described hereinafter and expressed in units of g fluid as absorbed per gram material per second (g/g/sec), relate to the ability of an absorbent material, and especially of a polymeric superabsorbent material, to imbibe liquid under no confining pressure conditions. Thus, such rates can be impacted by the specific, liquid accessible surface area, such as can be impacted by the particle size, shape, porosity, by the wetting properties of the material in relation to the liquid, and by the distribution of liquid within the material. Suitable materials can exhibit values in the range of more than about 0.02 g/g/sec and up to about 1 g/g/sec, and a range of commercially available materials exhibit more than about 0.2 g/g/sec and less than about 0.8 g/g/sec, often between about 0.4 g/g/sec and about 0.6 g/g/sec.

When incorporated into absorbent structures according to the present invention, materials exhibiting a slow free swelling behavior can have a particular advantageous effect, i.e. when the FRS is less than 0.4 g/g/sec, or even less than 0.2 g/g/sec or even as low as less than 0.05 g/g/sec.

A further way to include such materials is to design the article such that a relatively slow absorbing superabsorbent material is positioned relatively close to the loading point (i.e. in the crotch zone), whilst a faster absorbing material is positioned towards the ends of the structure (i.e. towards the waist regions when positioned on a wearer).

In addition to such superabsorbent materials, other materials suitable to create a permeable structures/members for the fluid storage regions are well known in the art, and many therefrom can be used to create a suitable structure, provided the above mentioned parameter are satisfied.

In measuring the concentration of hydrogel-forming absorbent polymer in a given region of an absorbent member, the percent by weight of the hydrogel-forming polymer relative to the combined weight of hydrogel-forming polymer and any other components (e.g., fibers, thermoplastic material, etc.) that are present in the region containing the polymer is used. With this in mind, the concentration of the hydrogel-forming absorbent polymers in a given region of an absorbent member according to the present invention can be in the range of from about 60 to 100%, preferably from about 70 to 100%, more preferably from about 80 to 100%, and most preferably from about 90% to 100%.

Whilst materials as described in the above can satisfy the requirements as such (e.g. a pure hydrogel forming material, or a pure foam material), preferred members for being used as storage absorbent member comprise two or more of the materials. This allows often to utilize materials which on their own do not satisfy the criteria, but the combination does.

The principle function of such fluid storage members is to absorb the discharged body fluid either directly or from other absorbent members (e.g., fluid acquisition/distribution members), and then retain such fluid, even when subjected to pressures normally encountered as a result of the wearer's movements.

The amount of hydrogel-forming absorbent polymer contained in the absorbent member may vary significantly. Furthermore, the concentration of hydrogel may vary throughout a given member. In other words, a member may have regions of relatively higher and relatively lower hydrogel concentration.

As another example of a material that will provide integrity of the mixture, in absorbent members comprising a blend of hydrogel-forming polymer and particulate polymeric foam, the member can comprise a thermoplastic material. Upon melting, at least a portion of this thermoplastic material migrates to the intersections of the respective member components, typically due to interparticle or interfiber capillary gradients. These intersections become bond sites for the thermoplastic material. When cooled, the thermoplastic materials at these intersections solidify to form the bond sites that hold the matrix of materials together.

Optional thermoplastic materials useful herein can be in any of a variety of forms including particulates, fibers, or combinations of particulates and fibers, such as further exemplified in the above mentioned reference of PCT U.S. Ser. No. 98/08515.

Storage Region and Distribution Region Interactions

Whilst the properties of the individual regions have been described in detail in the above, there are further requirements, which have to be adjusted in one region depending on the other region. Thus, the storage region can be described by having a certain basis capacity, which should be selected such that liquid as being released form the distribution region under certain pressure conditions has to be re-captured by the storage region (through which the liquid passed through before on its flow path). This effect has been discussed in the above, with regard to the desired compressibility of the distribution layer material. For any given compressibility, the will be a corresponding amount of liquid pressed out per unit area, depending on the basis weight of said material, i.e. the thicker the compressed material is, the more liquid will be squeezed out. It is now a requirement for the liquid storage layer to be able to absorb at least this amount of liquid, such that the "basis capacity" of the storage material should be higher than the "squeeze out liquid release". Basis capacity, can, for example, for superabsorbent/fluff mixtures, adjusted by selecting appropriate materials and concentrations.

Other Fluid Handling Member Components and Materials

In addition to the above described fluid distribution and fluid storage member, articles according to the present invention can comprise further fluid handling members and other components.

In particular, there can be members positioned between the topsheet and the storage region which aim at improving the acquisition functionality of the absorbent article, with regard to urine, and or to feces. Such members are well known to the person skilled in the art in the form of fibrous layers, or open pore foam regions, or and are described such as in our cases CM1096, EP Application No. 96111895.7, CM1453, PCT Application No. PCT/US97/05046, CM1640, PCT Application No. PCT/US97/20842, CM1642, PCT Application No. PCT/US97/20840, CM1643, PCT Application No. PCT/US97/20701, CM1809, EP Application No. 98110154.6, CM1879, EP Application No. 98114190.6, all of which are incorporated herein by reference.

Articles according to the present invention may also include pockets for receiving and containing waste, spacers which provide voids for waste, barriers for limiting the movement of waste in the article, compartments or voids which accept and contain waste materials deposited in the diaper, and the like, or any combinations thereof. Examples of pockets and spacers for use in absorbent products are described in U.S. Pat. No. 5,514,121 issued to Roe et al. on May 7, 1996, entitled "Diaper Having Expulsive Spacer"; U.S. Pat. No. 5,171,236 issued to Dreier et al. on Dec. 15, 1992, entitled "Disposable Absorbent Article Having Core Spacers"; U.S. Pat. No. 5,397,318 issued to Dreier on Mar. 14, 1995, entitled "Absorbent Article Having A Pocket Cuff"; U.S. Pat. No. 5,540,671 issued to Dreier on Jul. 30, 1996, entitled "Absorbent Article Having A Pocket Cuff With An Apex"; and PCT Application WO 93/25172 published Dec. 3, 1993, entitled "Spacers For Use In Hygienic Absorbent Articles And Disposable Absorbent Articles Having Such Spacer"; and U.S. Pat. 5,306,266, entitled "Flexible Spacers For Use In Disposable Absorbent Articles", issued to Freeland on Apr. 26, 1994. Examples of compartments or voids are disclosed in U.S. Pat. No. 4,968,312, entitled "Disposable Fecal Compartmenting Diaper", issued to Khan on Nov. 6, 1990; U.S. Pat. No. 4,990,147, entitled "Absorbent Article With Elastic Liner For Waste Material Isolation", issued to Freeland on Feb. 5, 1991; U.S. Pat. No. 5,62,840, entitled "Disposable Diapers", issued to Holt et al on Nov. 5, 1991; and U.S. Pat. No. 5,269,755 entitled "Trisection Topsheets For Disposable Absorbent Articles And Disposable Absorbent Articles Having Such Trisection Topsheets", issued to Freeland et al on Dec. 14, 1993. Examples of suitable transverse barriers are described in U.S. Pat. No. 5,554,142 entitled "Absorbent Article Having Multiple Effective Height Transverse Partition" issued Sep. 10, 1996 in the name of Dreier et al.; PCT Patent WO 94/14395 entitled "Absorbent Article Having An Upstanding Transverse Partition" published Jul. 7, 1994 in the name of Freeland, et al.; and U.S. Pat. No. 5,653,703 Absorbent Article Having Angular Upstanding Transverse Partition, issued Aug. 5, 1997 to Roe, et al. All of the above-cited references are hereby incorporated by reference herein.

Storage absorbent members according to the present invention can include other optional components that can be present in absorbent webs. For example, a reinforcing scrim can be positioned within the storage absorbent member, or between the respective absorbent members of the absorbent core. Such reinforcing scrims should be of such configuration as to not form interfacial barriers to liquid transfer, especially if positioned between the respective absorbent members of the absorbent core. In addition, several binders may be used to provide dry and wet integrity to the absorbent core and/or the absorbent storage member itself. In particular, hydrophilic glue fibers may be used. It is preferred that the amount of binder used is as low as possible, so as not to impair the capillary sorption properties of the absorbent member. However, the skilled artisan will recognize that there are also binders that may enhance the capillary sorption properties of the absorbent member such as fiberized hydrophilic glue with sufficiently high surface area. In this case, the high surface area hydrophilic glue may provide both the liquid handling function and the integrity function, in one material. Also, the respective absorbent member, or the entire absorbent core, can be enveloped within a liquid pervious sheet, such as a tissue paper sheet, to obviate user concern regarding loose particulate absorbent polymer, as long as the capillary continuity is not disturbed.

Other optional components that can be included are materials to control odor, contain fecal matter, etc. Also, any absorbent member comprising particulate osmotic absorbent or high surface area material, or the entire absorbent core, can be enveloped within a liquid pervious sheet, such as a tissue paper sheet, to obviate user concern regarding loose particulate absorbent polymer.

When integrity is introduced via a binder material, suitable binders are melt-blown adhesives such as those described in U.S. Pat. No. 5,560,878, issued Oct. 1, 1996 to Dragoo et al., the disclosure of which is incorporated herein by reference. Processes for combining melt-blown adhesives with the requisite hydrogel-forming polymer and high surface area material is also described in detail in the '878 patent.

The detailed description of making suitable samples is described in more detail in the above mentioned description of the PCT application titled "Absorbent Articles with Distribution Materials positioned underneath storage materials" filed in the name of the present applicant on Apr. 28, 1998 as PCT application U.S. Ser. No. 98/08515, which is incorporated herein by reference.

Reference is further made to the description of detailed test methods therein, namely for the Vertical Wicking Flux test, the Saline Flow Conductivity (SFC), and the Liquid Permeability tests, the liquid viscosity determination, and the determination of design Capacities. For II tests the described test conditions have to be met, too.

In addition to theses tests, the Performance of the articles can be well assessed by the "Post-Acquisition Collagen Rewet" test, wherein an article or an absorbent structure is first loaded in an Acquisition test protocol, and thereafter submitted to a particular rewet protocol.

Acquisition Test

This test should be carried out at about 22+/−2° C. and at 35+/−15% relative humidity. The synthetic urine used in these test methods is commonly known as Jayco SynUrine and is available from Jayco Pharmaceuticals Company of Camp Hill, Pennsylvania. The formula for the synthetic urine is: 2.0 g/l of KCl; 2.0 g/l of $Na_2SO_4$; 0.85 g/l of $(NH_4)H_2PO_4$; 0.15 g/l $(NH_4)H_2PO_4$; 0.19 g/l of $CaCl_2$; ad 0.23 g/l of $MgCl_2$. All of the chemicals are of reagent grade. The pH of the synthetic Urine is in the range of 6.0 to 6.4.

Figure 2:
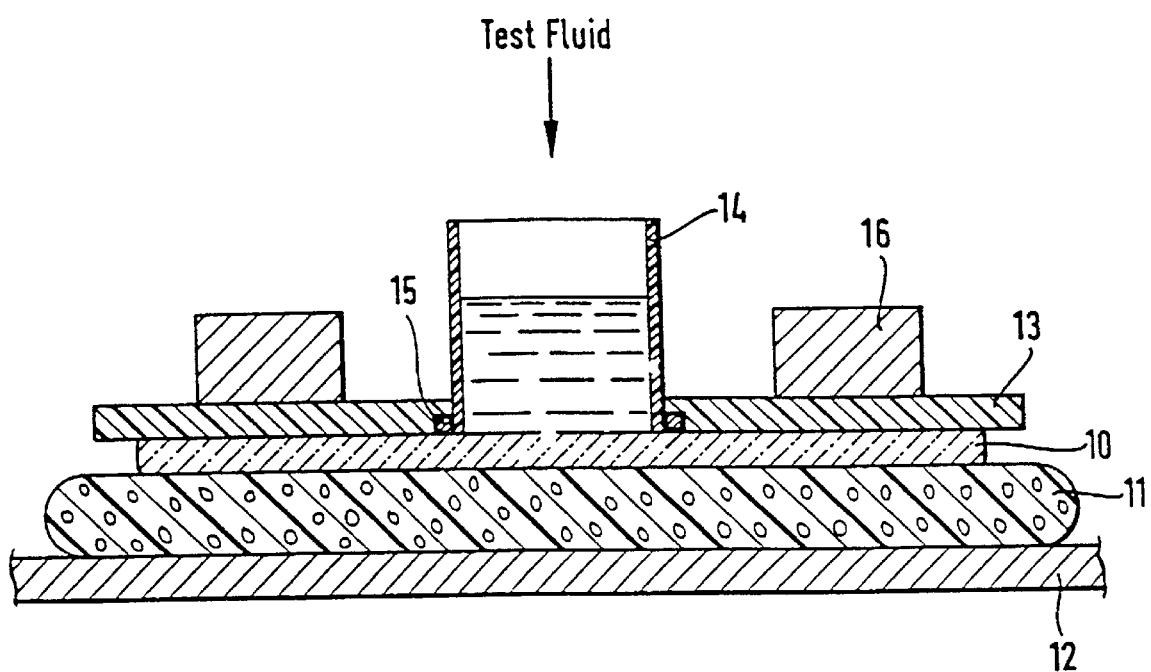
FIG. 2—Acquisition test stand

Referring to FIG. 2, an absorbent structure 910 is loaded with a 75 ml gush of synthetic urine at a rate of 15 ml/s using a pump (such as Model 7520-00,supplied by Cole Parmer Instruments., Chicago, U.S.A.), from a height of 5 cm above the sample surface. The time to absorb the urine is recorded by a timer. The gush is repeated at precisely 5 minute gush intervals until the article is sufficiently loaded. Current test data are generated by loading four times.

The test sample, which can be a complete absorbent article or an absorbent structure comprising an absorbent core, a topsheet, and a backsheet, is arranged to lie flat on a foam platform 911 within a perspex box (only base 912 of which is shown). A perspex plate 913 having a 5 cm diameter opening in its middle is placed on top of the sample on the loading zone of the structure. Synthetic urine is introduced to the sample through a cylinder 914 fitted, and glued into the opening. Electrodes 915 are located on the lowest surface of the plate, in contact with the surface of the absorbent structure 910. The electrodes are connected to the timer. Loads 916 are placed on top of the plate to simulate, for example a baby's weight. A pressure of about 50 g cm-2 (0.7 psi) is achieved by positioning weights 916, e.g. for the commonly available MAXI size 20 kg.

As test fluid is introduced into the cylinder it typically builds up on top of the absorbent structure thereby completing an electrical circuit between the electrodes. The test fluid is transported from the pump to the test assembly by means of a tubing of about 8 mm diameter, which is kept filled with test fluid. Thus the fluid starts to leave the tubing essentially at the same time the pump starts operating. At this time, also the timer is started, and the timer is stopped when the absorbent structure has absorbed the gush of urine, and the electrical contact between the electrodes is broken.

The acquisition rate is defined as the gush volume absorbed (ml) per unit time(s). The acquisition rate is calculated for each gush introduced into the sample. Of particular interest in view of the current invention are the first and the last of the four gushes.

This test is primarily designed to evaluate products generally referred to as MAXI size products for a design capacity of about 300 ml, and having a respective Ultimate Storage Capacity of about 300 ml to 400 ml. If products with significantly different capacities should be evaluated (such as can be envisaged for adult incontinence products or for smaller babies), the settings in particular of the fluid volume per gush should be adjusted appropriately to about 20% of the total article design capacity, and the deviation from the standard test protocol should be recorded.

Figure 3:
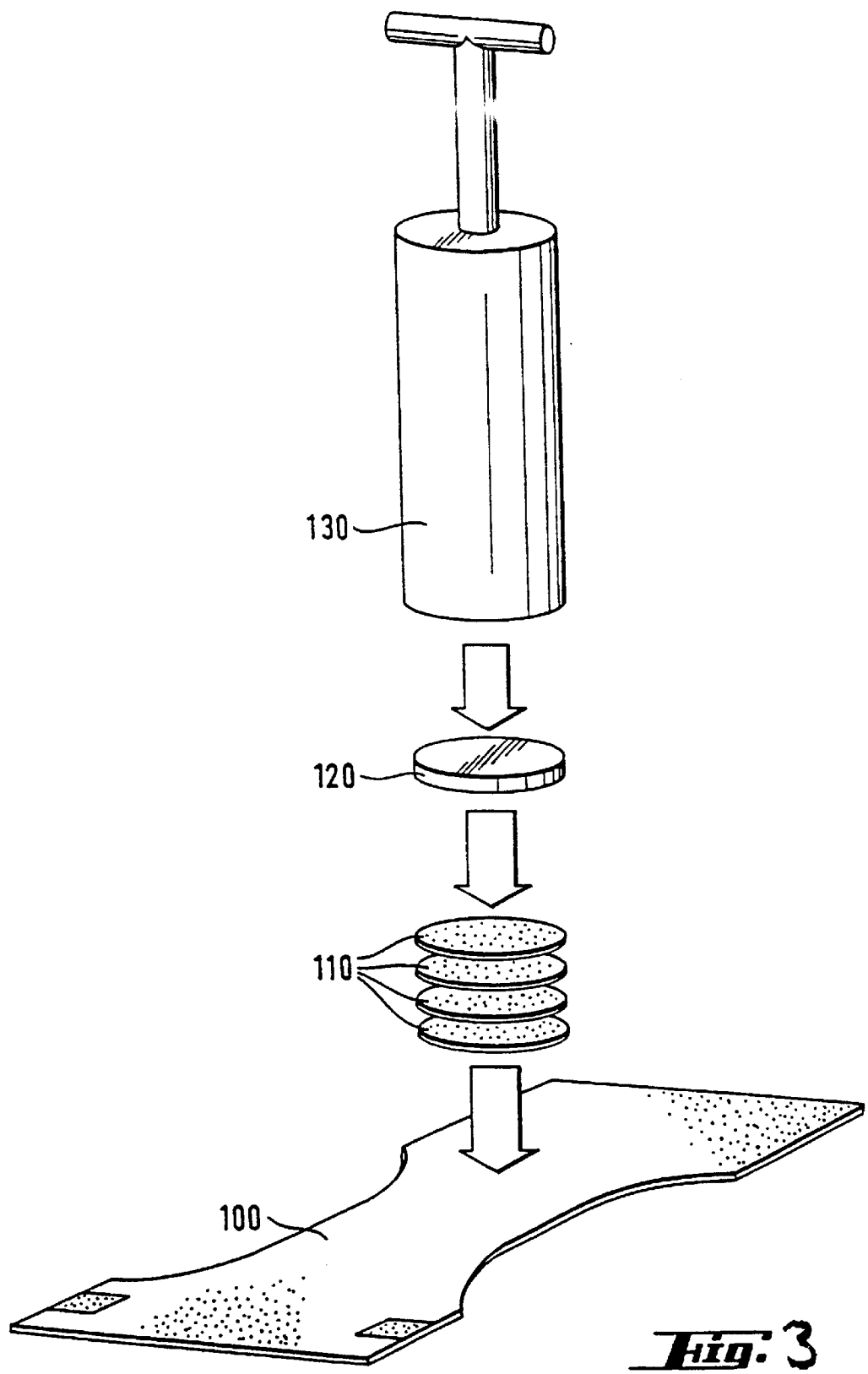
FIG. 3—Post Acquisition Collagen Rewet Method (PACORM) Test stand

Post Acquisition Collagen Rewet Method (refer to FIG. 3)

Before executing the test, the collagen film as purchased from NATURIN GmbH, Weinhein, Germany, under the designation of COFFI (or equivalent) and at a basis weight of about 28 g/m$^2$ is prepared by being cut into sheets of 90 mm diameter e.g. by using a sample cutter device, and by equilibrating the film in the controlled environment of the test room (see above) for at least 12 hours (tweezers are to be used for all handling of the collagen film).

At least 5 minutes, but not more than 6 minutes after the last gush of the above acquisition test is absorbed, the cover plate and weights are removed, and the test sample 1020 is carefully placed flat on a lab bench.

4 sheets of the precut and equilibrated collagen material 1010 are weighed with at least one milligram accuracy, and then positioned centered onto the loading point of the article, and covered by perspex plate 1030 of 90 mm diameter, and about 20 mm thickness. A weight 1040 of 15 kg is carefully added (also centred). After 30+/−2 seconds the weight and perspex plate are carefully removed again, and the collagen films are reweighed.

The Post Acquisition Collagen Rewet Method result is the moisture pick up of the collagen film, expressed in mg.

It should be noted further, that this testing protocol can be adjusted easily according to specific product types, such as different baby diaper sizes, or adult incontinence articles, or catamenial articles, or by the variation in the type and amount of loading fluid, the amount and size of the absorbent material, or by variations in the applicable pressure. Having once defined these relevant parameters, such modifications will be obvious to one skilled in the art. When considering the results from the adjusted test protocol the products can easily be optimising these identified relevant parameter such as in a designed experiment according to standard statistical methods with realistic in use boundary conditions.

Compression Under Load Determination

An important mechanical feature of the absorbent polymeric foams useful in the present invention, whether collapsible or non-collapsible, is their strength in their expanded state, as determined by its resistance to compression deflection (RTCD). The RTCD exhibited by the foams is a function of the polymer modulus, as well as the density and structure of the foam network. The polymer modulus is, in turn, determined by: a) the polymer composition; b) the conditions under which the foam is polymerized (for example, the completeness of polymerization obtained, specifically with respect to crosslinking); and c) the extent to which the polymer is plasticized by residual material, e.g., emulsifiers, left in the foam structure after processing.

To be useful as absorbents in absorbent articles such as diapers, the foams of the present invention must be suitably resistant to deformation or compression by forces encountered in use when such absorbent materials are engaged in the absorption and retention of fluids. Foams which do not possess sufficient foam strength in terms of RTCD may be able to acquire and store acceptable amounts of body fluid under no-load conditions but will too easily give up such fluid under the compressive stress caused by the motion and activity of the user of the absorbent articles that contain the foam.

The RTCD exhibited by the polymeric foams useful herein can be quantified by determining the amount of strain produced in a sample of saturated foam held under a certain confining pressure for a specified temperature and period of time. The method for carrying out this particular type of test is described in the TEST METHODS section of PCT publication WO 96/2168. Foams useful as absorbents are those which exhibit a RTCD such that a confining pressure of 5.1 kPa (0.74 psi) produces a strain of preferably less than 75% typically about 50% or less compression of the foam structure when it has been saturated to its free absorbent capacity with synthetic urine having a surface tension of 65±5 dynes/cm. Preferably the strain produced under such conditions will be in the range from about 2 to about 25%, more preferably from about 2 to about 15%, most preferably from about 2 to about 10%.

Free Swell Rate Method

This method determines the speed of superabsorbent materials, especially polymeric hydrogellingimaterials, such as cross-linked poly-acrylates to swell in synthetic urine of the Jayco type,as detailed in the General Section for test methods. The measurement principle is to allow superabsorbent material to absorb a known amount of fluid, and the time take to absorb the fluid is measured. The result is then expressed in gram of absorbed fluid per gram of material per second.

Test samples can be tested at their "as is" moisture, however, it is preferred to have these equilibrated under laboratory conditions for two days in a dessicator, using drierite (calcium sulfate or silica gel) or equivalent.

About 1 g (+/−0.1 g) of the test specimen are weighed to an accuracy of +/0.0001 g into a 25 ml beaker, which has 32 to 34 mm diameter, and 50 mm height. The material is evenly spread over the bottom. 20 ml of synthetic urine are weighed to an accuracy of +/−0.01 g in a 50 ml beaker, and are then poured carefully but quickly into, the beaker containing the test material. A timer is started immediately upon the liquid contacting the material. The beaker is not moved, or agitated during swelling.

The timer is stopped, and the time recorded to the nearest second (or more accurately if appropriate), when the last part of undisturbed fluid is reached by the swelling particles. In order to increase the reproducibility of the determination of the end point, the liquid surface can be illuminated by a small lamp without heating the surface by, that lamp. The beaker is re-weighed to monitor the actually picked up liquid.

The result is calculated by dividing the amount of actually picked up liquid by the time required for this pick up, and is expressed in "g/g/sec". The method should be repeated as required to ensure reproducibility.

If the test material has an increased moisture content, this can be incorporated into the result by dividing the grams of fluid by grams of dry absorbent material per second, or it can be considered by carefully drying the material under mild conditions like vacuum, and then measuring according to the above procedure. In all cases, results should be reported accordingly, in the absence of any specification, the test is run with an undried material of less than 10% moisture content, and reported "as is".

What is claimed is:

1. Absorbent article, having a fluid receiving surface oriented towards the wearer during use, and a garment oriented surface opposite said fluid receiving surface, said article comprising an ultimate fluid storage region, and a fluid distribution region positioned between said ultimate fluid storage region and said garment oriented surface, and in fluid communication with said ultimate fluid storage region wherein said ultimate fluid storage region and said fluid distribution region have substantially the same x-dimension, characterized in that said article has a rewet value of less than 150 mg when submitted to the PACoRM test, and in that said ultimate fluid storage region comprises ultimate fluid storage material which has a Capillary Sorption Desorption Capacity at 100 cm (CSDC 100) of at least 10 g/g; and said fluid distribution region comprises fluid distribution material having a Capillary Sorption Absorption Height at 30% of its maximum capacity (CSAH 30) of at least 25 cm, said absorbent article further comprising an absorbent core, and having a total ultimate storage capacity, further wherein said core comprises an ultimate liquid storage material providing at least 60% of said total ultimate storage capacity of said absorbent core.

2. Absorbent article according to claim 1, having a rewet value of less than 120 mg when submitted to the PACoRM test.

3. Absorbent article according to claim 1, wherein said ultimate fluid storage material has a CSDC 100 value of more than 20 g/g.

4. Absorbent article according to claim 1, wherein said storage region has a SFC value of more than $25 \times 10^{-7}$ cm$^3$sec/g.

5. Absorbent article according to claim 1, wherein said storage region has an in-plane permeability value of at least 10 Darcy.

6. Absorbent article according to claim 1, wherein said fluid distribution material has a CSAH 30 of at least 50 cm.

7. Absorbent article according to claim 1, having a crotch region, wherein in the crotch region said fluid distribution material has a permeability value at 50% saturation (k(50)), which is at least 15% of the permeability value at 100% saturation (k(100)).

8. Absorbent article according to claim 1, wherein said fluid distribution material has a permeability at 100% saturation (k(100)) of at least 1 Darcy.

9. Absorbent article according to claim 1, wherein said fluid distribution material has an expansion factor of at least 4.

10. An absorbent article according to claim 1, wherein said fluid distribution region comprises foam material.

11. An absorbent article according to claim 10, wherein said foam material is a polymeric foam material.

12. An absorbent article according to claim 11, wherein said polymeric foam material is derived from high internal phase water-in-oil emulsions.

13. An absorbent article according to claim 11, wherein said polymeric foam material has a compression under a load of 5.2 kPa (0.74 psi) of less than 75%.

14. An absorbent article according to claim 10, having a distribution region, wherein said distribution region foam material is non-uniform material.

15. An absorbent article according to claim 14, wherein said non-uniform material has non-uniform properties, which are selected from the group of pore size, hydrophilicity, compression under load, and CSDC, and CSAC at corresponding heights.

16. An absorbent article according to claim 1, wherein the fluid distribution region comprises fibrous material.

17. An absorbent article according to claim 1, wherein said ultimate fluid storage region comprises fibrous material.

18. An absorbent article according to claim 1, wherein said ultimate fluid storage region comprises superabsorbent material.

19. An absorbent article according to claim 18, wherein said ultimate fluid storage region comprises from about 50% by weight superabsorbent material.

20. An absorbent article according to claim 18, wherein said ultimate fluid storage region comprises bonding means for said superabsorbent material, said bonding means being selected from the group consisting of hydrophillic glue fibers and melt-blown adhesive.

21. An absorbent article according to claim 18, wherein said ultimate fluid storage region comprises superabsorbent material having a SFC of at least $50 \times 10^{-7}$ cm$^3$sec/g.

22. An absorbent article according to claim 18, wherein said ultimate fluid storage region comprises superabsorbent material having a Free Swell Rate of less than 0.4 g/g sec.

23. An absorbent article according to any of claim 18, wherein said ultimate fluid storage region comprises superabsorbent material of the mixed-bed ion exchange type.

24. An absorbent article according to claim 1, wherein said ultimate fluid storage region is essentially free of void, apertures, or gaps having an individual void, aperture or gap volume of more than 10 mm$^3$.

25. Absorbent article according to claim 1, having a crotch region, whereby the crotch region has a lower ultimate fluid storage capability than one or more waist region (s) together.

26. An absorbent article according to claim 25, comprising an absorbent core, and having a crotch width, wherein the crotch width of the absorbent core is not greater than 7.5 cm (3 inch).

27. Absorbent article according to claim 1 wherein average basis weight of the ultimate fluid storage material is less than 450 g/m$^2$.

* * * * *